United States Patent [19]

Nauta

[11] 3,998,874
[45] Dec. 21, 1976

[54] PHENYLENE DI-ETHERS

[75] Inventor: Wijbe Thomas Nauta, Nieuw-Loosdrecht, Netherlands

[73] Assignee: Gist-Brocades N.V., Netherlands

[22] Filed: Feb. 1, 1974

[21] Appl. No.: 438,765

Related U.S. Application Data

[63] Continuation-in-part of Ser. No. 127,382, March 23, 1971, abandoned.

[52] U.S. Cl. .................. 260/501.17; 260/348 R; 260/570.7; 260/612 D; 260/625; 424/316; 424/330
[51] Int. Cl.² .......................... C07C 93/06
[58] Field of Search .............. 260/570.7, 501.18; 424/330

[56] References Cited

UNITED STATES PATENTS

| | | | |
|---|---|---|---|
| 3,033,640 | 5/1962 | Hofer et al. | 260/570.7 X |
| 3,432,545 | 3/1969 | Hoove | 260/570.7 X |
| 3,555,161 | 1/1971 | Brandstrom et al. | 260/570.7 X |
| 3,872,147 | 3/1975 | Koppe et al. | 260/570.7 X |

OTHER PUBLICATIONS

Terentev et al., "Chemical Abstracts", vol. 57, pp. 16455–16456 (1962).

Primary Examiner—Robert V. Hines
Attorney, Agent, or Firm—Robert E. Burns; Emmanuel J. Lobato; Bruce L. Adams

[57] ABSTRACT

Substituted phenylene di-ethers of the formula;

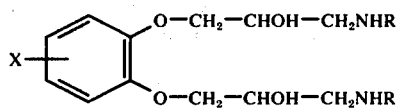

wherein R represents an isopropyl or tertiary butyl group and X represents hydrogen or lower alkyl, and acid addition salts thereof.

The compounds are useful anti-arrhythmic agents and also show local anaesthetic activity in mammals. Their methods of preparation are disclosed and also pharmacological preparations containing the same.

8 Claims, No Drawings

PHENYLENE DI-ETHERS

This is a continuation-in-part of Ser. No. 127,382, filed Mar. 23, 1971 and now abandoned.

BRIEF DESCRIPTION OF THE INVENTION

The new ethers of the invention are the phenylene di-ethers of the general formula

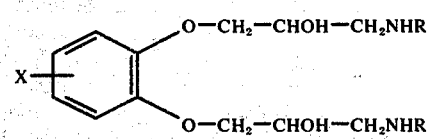

wherein R represents an isopropyl or tertiary butyl group and X represents hydrogen or lower alkyl, and acid addition salts thereof. The term "lower" as applied herein to alkyl indicates that the group contains a straight or branched hydrocarbon chain with at most 6 carbon atoms.

The phenylene di-ethers of formula I have valuable therapeutic properties. They have pronounced anti-arrhythmic properties and, in addition, show $\beta$-sympatholytic and local anaesthetic activities. Preferred compounds are those wherein X is a lower alkyl group. The most preferred compound is 1,1-[(3-isopropyl-o-pheylene)dioxy]-bis-[3-(isopropylamino)-propan-2-ol] and its acid addition salts. For use as therapeutics the compounds of formula I may be used as bases or as acid addition salts containing pharmaceutically acceptable non-toxic anions e.g. the hydrohalides, sulphates, oxalates, tartrates, fumarates, acetates, citrates, maleates, succinates, lactates and pamoates. The bases or non-toxic acid addition salts thereof may be administered orally or parenterally in a pharmacologically acceptable carrier according to accepted pharmaceutical practice. The dosage will depend on the mammalian species treated. For application as anti-arrhythmics and $\beta$-sympatholytics in adult mammals, the oral dosage will be from 5 to 100 mg. daily.

In comparison to known aminopropan-2-ol ethers the phenylene di-ethers of formula I are strong anti-arrhythmics and relatively weak $\beta$-sympatholytics.

The $\beta$-adrenergic blocking activity was determined on the guinea pig tracheal chain prepared as described by H. Timmerman and N. G. Scheffer, J. Pharm. Pharmacol. 20, 78 (1968) by measuring the relaxation caused by cumulative doses of isoprenaline, both in absence and presence of the test compound, using the method of J. M. van Rossum, Arch. Int. Pharmacodyn. Ther. 143, 299 (1963). The antagonism to the cardiac $\beta$-receptors was estimated as described by V. S. V. Subbu, Med. Pharmacol. Exp. 16, 119 (1967) on the isolated, spontaneously beating, right atrium of the guinea pig, by measuring the antagonism towards the positive chronotropism caused by cumulative doses of isoprenaline. The pA2-values were calculated according to Van Rossum from the parallel shift to the right of the log dose - response curves.

The anti-arrhythmic activity in vitro was determined as follows. Right atrial muscles from guinea pigs were dissected and freed from the appendage. They were suspended in 100 ml of a modified Ringer-Locke solution (g/l: NaCl 7.30, KCl 0.42, $CaCl_2$ 0.24, $NaHCO_3$ 2.10, glucose 0.20) at 37° C and aerated with 5% $CO_2$ in oxygen. The pH of the solution was 7.4. Spontaneous contractions were recorded on a Schwarzer ECG (Cardioscript III) using an Endevco Pixie Transducer (8101) in a Wheatstone bridge circuit. Tension was so adjusted that contractions reached maximal amplitude while keeping distortion of the baseline minimal. After a 40-min equilibrium period the test compound was added and for 30 minutes contractile force and rate were recorded at 1-min intervals for 10 seconds. Next, ouabain was added in a concentration of 0.5 $\mu$g/ml and force and rate were measured at 1-min intervals over a 60-min period. The minimal drug concentration, necessary to prevent any form of arrhythmia, was determined using concentrations of 1, 2, 3, 5, 7 and 10 times $10^{-x}$ M in this or the reversed sequence till the limit concentration was reached at which the pattern remained regular. This was confirmed at least once. Control experiments without test compounds were carried out daily.

The results are shown in the following table (R = isopropyl).

TABLE I

| Compound | X | $\beta$-adrenergic blocking act. pA2 trachea | pA2 atrium | Antiarrh. act. −log min. dose |
|---|---|---|---|---|
| A | H | 6.73 (±0.05) | 6.49 (±0.07) | 3.70 |
| B | 3-$CH_3$ | 5.80 (±0.08) | 5.48 (±0.12) | 4.70 |
| C | 3-$iC_3H_7$ | 5.35 (±0.11) | 4.59 (±0.13) | 5.00 |
| D | 4-$CH_3$ | 6.66 (±0.09) | 6.22 (±0.06) | 4.30 |
| E | 4-$iC_3H_7$ | 6.48 (±0.09) | 5.64 (±0.15) | 4.70 |
| G*) | — | 7.61 (±0.03) | 9.01 (+0.16) | 3.52 |

*)1-(isopropylamino)-3-phenoxy-2-propanol.

The mono-ether, G, is a known pharmacologically active compound (V. Petrow et al., J. Pharm. and Pharmacol. 8, 666 (1956)).

It appears from the table that the anti-arrhythmic activity of the new compounds is stronger than that of the mono-ether G and that the $\beta$-sympatholytic activity is much weaker, especially on the atrium. It can therefore be concluded that the strong anti-arhythmic activity of the new di-ethers cannot be attributed to their $\beta$-sympatholytic activity. This is confirmed by their in vivo antagonism of aconitineinduced arrhythmias. This test was carried out in male rats under urethane anaesthesia as described by B. Vargaftig and J. L. Coignet, Eur. J. Pharmacol., 6, 49 (1969). It was estimated what dose of aconitine in an i.v. infusion (5 $\mu$g/kg/min, rate 0.2 ml/min) would induce arrhythmias. Three minutes before the infusion physiological saline with or without test compound was injected i.v.

The results are listed in the following table.

TABLE II

| Compound | X | R | Dose mg/kg | Dose of aconitine $\mu$g/kg | % protection |
|---|---|---|---|---|---|
| Control | — | — | — | 27.9 | — |
| A | H | i-$C_3H_7$ | 4 | 31.5 | 12.9 |
|  |  |  | 8 | 37.8 | 35.5 |
|  |  |  | 16 | 58.8 | 110.8 |
| Control | — | — | — | 31.8 | — |
| C | 3-i$C_3H_7$ | i-$C_3H_7$ | 0.5 | 45.8 | 44.0 |

TABLE II-continued

| Compound | X | R | Dose mg/kg | Dose of aconitine µg/kg | % protection |
|---|---|---|---|---|---|
| | | | 1.0 | 57.1 | 79.6 |
| | | | 2.0 | 74.9 | 135.5 |
| Control | — | — | — | 24 | — |
| F | H | t-C$_4$H$_9$ | 4 | 34 | 41.7 |
| | | | 8 | 49 | 104.2 |
| | | | 16 | 62 | 158.6 |

It has been established that antagonism of aconitine-induced arrhythmias is not caused by β-adrenergic blocking activity (see for instance B. B. Vargaftig and J. L. Coignet, Thérapie 24, 853–58 (1966)). The low β-sympatholytic activity of the diethers implies that the compounds will now only be effective against arrhythmias caused by hyperadrenergic activity, but more generally against various forms of arrhythmias. Compounds with a strong β-sympatholytic activity may cause bronchospasms in cases where the adrenergic tone is maximum and they are therefore contraindicated in asthmatic patients (see for instance R. S. McNeill, Lancet, 1964, 1101–1102). Because of their low β-sympatholytic activity the di-ethers of the invention are not contra-indicated in asthmatic patients.

The phenylene di-ethers of formula I may be prepared by reacting a di(chlorohydrin) ether of the formula:

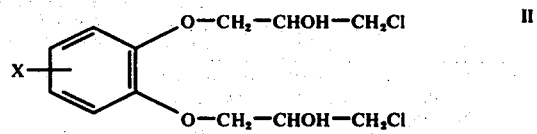

wherein X is as hereinbefore defined, with an amine of the formula NH$_2$R, wherein R is as hereinbefore defined. The reaction is preferably carried out by heating the reactants in an inert organic solvent, such as benzene, toluene or an alcohol (e.g. ethanol). The reaction temperature may range from 70° to 120° C and the reaction time from 3 to 30 hours. The best yields are obtained by heating the reactants in benzene in a closed vessel, e.g. a Carius tube, for 20 hours at 80° C with a sixfold excess of amine.

The starting materials of formula II may be prepared by reacting a phenylene di-alcohol of the formula:

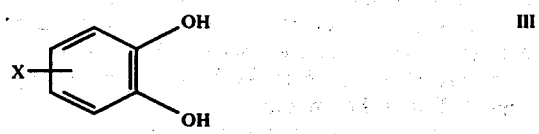

wherein X is as hereinbefore defined, with epichlorohydrin. Preferably the reactants are stirred together at moderate temperature for a long time (mostly some days) under an inert gas atmosphere in the presence of a small amount of a basic catalyst such as an alkali metal hydroxide (e.g. sodium hydroxide), a tertiary amine (e.g. triethylamine) or piperidine. Advantageously a four-to six-fold excess of epichlorohydrin is used.

According to another method the phenylene di-ethers of formula I are prepared by reacting a di(glycidyl) ether of the formula:

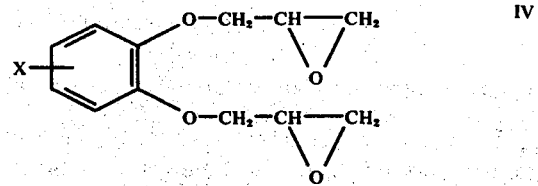

wherein X is as hereinbefore defined, with an amine of the formula NH$_2$R, wherein R is as hereinbefore defined. Preferred reaction conditions are the same as mentioned above for the reaction of a di(chlorohydrin) ether of formula II with an amine of the formula NH$_2$R.

The starting materials of formula IV may be prepared by reacting a di(chlorohydrin) ether of formula II with a base in the presence of epichlorohydrin. The reaction may be performed by adding the base to the reaction mixture obtained from the reaction between a phenylene di-alcohol of formula III and an excess of epichlorohydrin. Preferably aqueous solutions of alkali metal hydroxides, such as sodium hydroxide saturated with an alkali metal carbonate, such as sodium carbonate, are used. The reaction is perferably carried out by stirring the reactants at room temperature for several hours, e.g. one day. It will be understood that it is also possible to isolate and purify the di(chlorohydrin) ether before reacting it with a base and that the di(-glycidyl) ethers may also be obtained by reacting a phenylene di-alcohol of formula III with epichlorohydrin under the basic conditions needed to obtain a di(glycidyl) ether.

According to another method the phenylene di-ethers of formula I are prepared by reacting an alkali metal derivative of a phenylene di-alcohol of formula III with a compound of the formula;

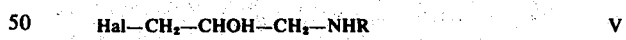

Hal—CH$_2$—CHOH—CH$_2$—NHR     V wherein Hal represents a halogen atom, and R is as hereinbefore defined. The reaction is preferably carried out by heating the reactants in an inert organic solvent such as benzene.

According to another method the phenylene di-ethers of formula I are prepared by reacting a phenylene di-alcohol of formula III, or an alkali metal derivative thereof, with a compound of the formula:

wherein R is as hereinbefore defined. The reaction is preferably carried out by heating the reactants in an inert organic solvent such as benzene. When a phenylene di-alcohol of formula III is employed as a starting material it is advantageous to add a base, e.g. an alkali metal hydroxide, such as sodium hydroxide.

According to another method the phenylene di-ethers of formula I are prepared by monoalkylating each of the primary amino groups of a compound of the formula:

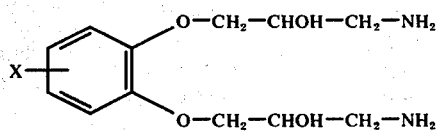  VII wherein X is as hereinbefore defined, by methods known per se for the alkylation with a radical R (as hereinbefore defined) of primary amines. The alkylation may be carried out by reacting the compound of formula VII with an alkyl halide of the formula Hal-R, wherein Hal and R are as hereinbefore defined, preferably by heating the reactants in an organic solvent, such as ethanol, in the presence of a base, e.g. sodium carbonate. When it is desired to obtain a phenylene di-ether product of formula I wherein R is an isopropyl group, the alkylation is preferably performed by reacting the compound of formula VII with acetone under reducing conditions. The use of platinum as a catalyst for the reduction with hydrogen is preferred. The reactant acetone may also serve as a solvent medium or a component of a solvent mixture also containing a low boiling alcohol such as methanol. The reaction is preferably carried out at ordinary or slightly elevated temperature.

The starting materials of formula VII may be prepared by reacting a di(glycidyl) ether of the formula IV with ammonia. The reaction is preferably carried out in an organic solvent, such as a lower aliphatic alcohol, e.g. methanol. Reaction temperatures from room temperature upwards can be employed, higher temperatures making it advisable to employ closed vessels wherein pressures surpassing ordinary pressure can be employed.

Acid addition salts of the phenylene di-ethers of formula I may be prepared by methods known per se. For example, the base may be treated with the equivalent amount of the acid in an invert solvent.

By the term "methods known per se" as used in the specification is meant methods heretofore used or described in the literature.

The following Examples illustrate the preparation of phenylene di-ethers according to the present invention.

EXAMPLE 1

Synthesis of
1,1'-(o-phenylenedioxy)-bis-[3-(isoproyl-amino)propan-2-ol] dihydrochloride 37.0 g. of epichlorohydrin are added under a nitrogen atmosphere to 11.0 g. of catechol. After the catechol is dissolved, a solution of 0.15 g of sodium hydroxide in a few drops of water is added dropwise and the temperature is raised to 40° C. At this temperature the reaction mixture is stirred for 48 hours, after which the remaining epichlorohydrin is distilled off under reduced pressure. The resulting oil is dissolved in chloroform, washed twice with water and distilled. 19.5 g. of 1,1'-(o-phenylenedioxy)-bis-(3-chloropropan-2-ol) are obtained with a boiling point of 153°–156° C./10$^{-2}$ –10$^{-3}$ mm.Hg. After crystallization from diethyl ether the melting point is 64°–66° C.

6.0 g. of 1,1'-(o-phenylenedioxy)-bis-(3-chloropropan-2-ol) are heated for 20 hours in a Carius tube at 80° C. in the presence of 3 ml. of benzene and 10 ml. of isopropylamine. The content of the tube is concentrated and the residue is taken up in 2N acetic acid and washed twice with chloroform. The amino ether is then liberated by adding 2N sodium hydroxide and extracted with chloroform. The chloroform solution is washed three times with water and concentrated by evaporation of solvent. There are obtained 6.0 g. of 1.1'-(o-phenylenedioxy)-bis-[3-(isopropylamino) propan-2-ol] with a purity of 9.34% (determined by titration with hydrocloric acid), from which a yield of 82.3% can be calculated.

The aminoether is dissolved in diethyl ether and converted into the dihydrochloride by addition of a calculated amount of an ethereal hydrogen chloride solution. The precipitated salt is filtered off, dried over phosphorus pentoxide and crystallized a few times from a mixture of anhydrous acetone and absolute ethanol. Its melting point is 114.5° – 116° C.

EXAMPLE 2

Synthesis of
1,1'-[(3-methyl-o-phenylene)dioxy]-bis-[3-(isopropylamino)propan-2-ol] dihydrochloride 18.7 g. of 3-methylcatechol, 56 g. of epichlorohydrin and 0.2 g. of sodium hydroxide, dissolved in a few drops of water, are stirred together under a nitrogen atmosphere for 6 days at 40° C. The remaining epichlorohydrin is distilled off under reduced pressure. The resulting oil is dissolved in chloroform, washed twice with water and purified by molecular distillation at 10$^{-3}$ mm.Hg. There are obtained 32.54 g. of impure 1,1'-[3-(methyl-o-phenylene)dioxy]-bis-(3-chloropropan-2-ol).

16 g. of the di-ether is heated in a Carius tube for 20 hours at 80° C in the presence of 3 ml. of benzene with a sixfold excess of isopropylamine. 11.8 g. of 1,1'-[(3-methyl-o-phenylene)dioxy]-bis-[3-isopropylamino)-propan-2-ol] are obtained in the form of an oil with a purity of 90.6%. The base is dissolved in diethyl ether and converted into the dihydrochloride by adding a calculated amount of an ethereal hydrogen chloride solution. After a few crystallizations from acetone and ethanol, the melting point of the dihydrochloride is 151°–152° C.

EXAMPLE 3

Synthesis of
1,1'-[(3-isopropyl-o-phenylene)dioxy]-bis-[3-(isopropylamino)-propan-2-ol] dihydrochloride 22.9 g. of 3-isopropylcatechol, 56 g. of epichlorhydrin and 0.2 g. of sodium hydroxide, dissolved in a few drops of water, are stirred together for 21 days at 40° C under a nitrogen atmosphere. The excess of epichlorohydrin is distilled off under reduced pressure. The resulting oil is dissolved in chloroform, washed twice with water and purified by molecular distillation at 10$^{-3}$ mm.Hg 32.55 g. of impure 1,1'-[(3-isopropyl-o-phenylene)dioxy]-bis-(3-chloropropan-2-ol) are obtained.

14.7 g. of the impure di-ethers are converted into the isopropylamine compound by the procedure described in Example 4. 7.80 g. of 1,1'-[(3-isopropyl-o- phenylene)dioxy]-bis-[3-(isopropylamino) propan-2-ol] are obtained with a purity of 84%. The impure product is dissolved in diethyl ether and treated with a calculated amount of ethereal hydrogen chloride to obtain the dihydrochloride. After a few crystallizations from a mixture of anhydrous acetone and absolute ethanol, its melting point is 166°–168° C.

EXAMPLE 4

Synthesis of 1,1'-[(4-methyl-o-phenylene)dioxy]-bis-[3-(isopropylamino)-propan-2-ol] dihydrochloride 12.4 g. of 4-methylcatechol, 37 g. of epichlorohydrin and 0.15 g. of sodium hydroxide, dissolved in a few drops of water, are stirred together for 48 hours at 40° C under nitrogen atmosphere. The excess of epichlorohydrin is distilled off under reduced pressure. The resulting oil is dissolved in chloroform, washed twice with water and purified by molecular distillation at $10^{-3}$ mm.Hg to yield 25.6 g. of impure 1,1'-[(4-methyl-o-phenylene)dioxy]-bis-(3-chloropropan-2-ol).

11.6 g. of this di-ether are converted into the isopropylamine compound by the procedure described in Example 2. 10.85 g. of 1,1'-[(4methyl-o-phenylene)dioxy]-bis-[3-(isopropylamino)-propan-2-ol] are obtained with a purity of 93.5%. The dihydrochloride is obtained by addition of the calculated amount of ethereal hydrogen chloride solution to a solution of the base in diethyl ether. The salt is crystallized from a mixture of anhydrous acetone and absolute ethanol; its melting point is 92.5°–95° C.

EXAMPLE 5

Synthesis of 1,1'-[(4-isopropyl-o-phenylene)dioxy]-bis-[3-(isopropylamino)-propan-2-ol] dihydrochloride 22.9 g. of 4-isopropylcatechol, 56 g. of epichlorohydrin and 0.2 g. of sodium hydroxide, dissolved in a few drops of water, are stirred together for 24 hours at 40° C. under a nitrogen atmosphere. The temperature is then lowered to 20° C. and 60 ml. of a 5N solution of sodium hydroxide, saturated with sodium carbonate, are added. The reaction mixture is vigorously stirred for 24 hours. The two layers are then separated and the aqueous layer is extracted twice with diethyl ether. The extracts are added to the organic layer, which is washed three times with water. The organic solution is concentrated by distilling off the solvent under reduced pressure. On further distillation 1,1'-[(4-isopropyl-o-phenylene)dioxy]-bis-(2,3-epoxy-propane) is obtained, boiling point 125°–130° C./$10^{-3}$ mm.Hg. Yield 76%. 10 g. of this diglycidyl ether are heated for 20 hours in a Carius tube at 80° C in the presence of 3 ml. of benzene with a sixfold excess of isopropylamine. The content of the tube is concentrated and the residue is taken up in 2N acetic acid and washed twice with chloroform. The amino ether is then liberated by adding 2N sodium hydroxide and extracted with chloroform. The chloroform solution is washed three times with water and concentrated by evaporation of solvent. 1,1'-[(4-isopropyl-o-phenylene)dioxy]-bis-[3-(isopropylamino) propan-2-ol] is obtained in a 77.9% yield. Its dihydrochloride is formed by addition of the calculated amount of an ethereal hydrogen chloride solution to a solution of the base in diethyl ether. After crystallization from anhydrous acetone the melting point of the dihydrochloride is 51°–55° C. The substance appears to be very hydroscopic.

EXAMPLE 6

Synthesis of 1,1'-(o-phenylenedioxy)-bis-[3-(tert.-butylamino)-propan-2-ol] dihydrochloride This compound was prepared by the method described in Example 5 with substitution of the isopropylamine by an equivalent amount of tert.-butylamine. The dihydrochloride was crystallized from a mixture of methanol, ethanol and aceton. Melting point 204°–206° C.

In a manner similar to that described in the preceding examples other phenylene di-ethers of formula I can be prepared. Examples of such compounds are 1,1'-[(3-ethyl-o-phenylene)dioxy]-bis-[3-(isopropylamino)-propan-2-ol],
1,1'-[(4-ethyl-o-phenylene)dioxy]-bis-[3-(isopropylamino)propan-2-ol],
1,1'-[(3-n-propyl-o-phenylene)dioxy]-bis-[3-isopropylamino)-propan-2-ol],
1,1'-[(4-n-propyl-o-phenylene)dioxy]-bis-[3-(isopropylamino)-propan-2-ol],
1,1'-[(3-n-butyl-o-phenylene)dioxy]-bis-[3-(isopropylamino)-propan-2-ol],
1,1'-[(4-n-butyl-o-phenylene)dioxy]-bis-[3-(isopropylamino)-propan-2-ol],
1,1'-[(3-tert.-butyl-o-phenylene)dioxy]-bis-[3-(isopropylamino)-propan-2-ol],
1,1'-[(4-tert.-butyl-o-phenylene)dioxy]-bis-[3-(isopropylamino)-propan-2-ol],
1,1'-[(3-methyl-o-phenylene)dioxy]-bis-[3-(tert.-butylamino)-propan-2-ol],
1,1'-[(4-methyl-o-phenylene)dioxy]-bis-[3-(tert.-butylamino)-propan-2-ol],
1,1'-[(3-ethyl-o-phenylene)dioxy]-bis-[3-(tert.-butylamino)-propan-2-ol],
1,1'-[(4-ethyl-o-phenylene)dioxy]-bis-[3-(tert-.butylamino)-propan-2-ol],
1,1'-[(3-n-propyl-o-phenylene)dioxy]-bis-[3-(tert.-butylamino)-propan-2-ol],
1,1'-[(4-n-propyl-o-phenylene)dioxy]-bis-[3-(tert.-butylamino)-propan-2-ol],
1,1'-[(3-isopropyl-o-phenylene)dioxy]-bis-[3-(tert.-butylamino)-propan-2-ol],
1,1'-[(4-isopropyl-o-phenylene)dioxy]-bis-[3-(tert.-butylamino)-propan-2-ol],
1,1'-[(3-n-butyl-o-phenylene)dioxy]-bis-[3-(tert.-butylamino)-propan-2-ol],
1,1'-[(4-n-butyl-o-phenylene)dioxy]-bis-[3-(tert.-butylamino)-propan-2-ol],
1,1'-[(3-tert.-butyl-o-phenylene)dioxy]-bis-[3-(tert.-butylamino)propan-2-ol],
1,1'-[(4-tert.-butyl-o-phenylene)dioxy]-bis-[3-(tert.-butylamino)propan-2-ol].

The phenylene di-alcohols of formula III, needed as a starting material for these compounds, are all known compounds.

The invention includes within its scope pharmaceutical preparations containing, as active ingredient, at least one of the therapeutically active compounds of general formula I, or non-toxic acid addition salt thereof, in association with a pharmacologically acceptable carrier. The preparations may take any of the forms customarily employed for administration of therapeutically active substances, but the preferred types are those suitable for oral administration and especially tablets, pills and capsules including the substance. The tablets and pills may be formulated in the usual manner with one or more pharmacologically acceptable diluents or excipients, for example lactose or starch, and include materials of a lubricating nature, for example calcium stearate. Capsules made of absorbable material, such as gelatin, may contain the active substance alone or in admixture with a solid or liquid diluent. Liquid preparations may be in the form of suspensions, emulsions, syrups or elixirs of the active substance in water or other liquid medium commonly used for making orally acceptable pharmaceutical formulations, such as liquid paraffin, or a syrup or elixir base. The active substance may also be made up in a form suitable for parenteral administration, i.e. as a suspension or emulsion in sterile water or an organic liquid usually employed for injectable preparations, for example a vegetable oil such as olive oil, or a sterile solution in an organic solvent.

The following Examples illustrate the preparation of a pharmaceutical composition according to the invention.

EXAMPLE 7

25 g of 1,1'-[(3-isopropyl-o-phenylene)dioxy]-bis-[3-(isopropylamino)propan-2-ol] dihydrochloride, 25 g of Avicel PH 101 (microcrystalline cellulose) and 1 g of Aerosil (highly purified silicon dioxide) are mixed together and gelatin capsules are filled each with 51 mg of the mixture so that each capsule contains 25 mg of active substance.

EXAMPLE 8

800 g of lactose and 200 g of maize starch are mixed with 200 ml of 5% maize starch in water. The mixture is granulated, dried at 55° C and sieved through a no. IV sieve (sieve opening 0.7 mm).

1000 g of the granulate are mixed with 100 g of 1,1'-[(3-isopropyl-o-phenylene)dioxy]-bis-[3-(isopropylamino)propan-2-ol] dihydrochloride and gelatin capsules are filled each with 110 mg of the mixture so that each capsule contains 10 mg of active substance.

What I claim and desire to secure by Letters Patent for:

1. A compound selected from the group consisting of phenylene di-ethers of the formula

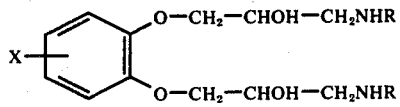

wherein R represents as isopropyl or tertiary butyl group and X represents hydrogen or lower alkyl and acid addition salts thereof.

2. A phenylene di-ether according to claim 1, wherein X is a lower alkyl group.

3. A phenylene di-ether according to claim 2, which is a compound selected from the group consisting of 1,1'-[(3-isopropyl-o-phenylene)dioxy]-bis-[3-(isopropylamino)propan-2-ol] and its acid addition salts.

4. A phenylene di-ether according to claim 2, which is a compound selected from the group consisting of 1,1'-[(3-methyl-o-phenylene)dioxy]-bis-[3-(isopropylamino)propan-2-ol] and its acid addition salts.

5. A phenylene di-ether according to claim 2, which is a compound selected from the group consisting of 1,1'-[(4-methyl-o-phenylene)dioxy]-bis-[3-(isopropylamino)propan-2-ol] and its acid addition salts.

6. A phenylene di-ether according to claim 2, which is a compound selected from the group consisting of 1,1'-[(4-isopropyl-o-phenylene)dioxy]-bis-[3-(isopropylamino)propan-2-ol] and its acid addition salts.

7. A phenylene di-ether according to claim 1, which is a compound selected from the group consisting of 1,1'-(o-phenylenedioxy)-bis-[3-(isopropylamino)propan-2-ol] and its acid addition salts.

8. A phenylene di-ether according to claim 1, which is a compound selected from the group consisting of 1,1'-(o-phenylenedioxy)-bis-[3-(tert.-butylamino)propan-2-ol] and its acid addition salts.

* * * * *